United States Patent
Kuritsyn et al.

(10) Patent No.: US 9,989,758 B2
(45) Date of Patent: Jun. 5, 2018

(54) DEBRIS PROTECTION SYSTEM FOR REFLECTIVE OPTIC UTILIZING GAS FLOW

(71) Applicant: KLA-Tencor Corporation, Milpitas, CA (US)

(72) Inventors: Alexey Kuritsyn, San Jose, CA (US); Alexander Bykanov, San Diego, CA (US); Oleg Khodykin, San Diego, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 292 days.

(21) Appl. No.: 14/247,082

(22) Filed: Apr. 7, 2014

(65) Prior Publication Data
US 2014/0306115 A1   Oct. 16, 2014

Related U.S. Application Data

(60) Provisional application No. 61/810,265, filed on Apr. 10, 2013.

(51) Int. Cl.
| | |
|---|---|
| *G01F 23/00* | (2006.01) |
| *G02B 27/00* | (2006.01) |
| *H05G 2/00* | (2006.01) |
| *G03F 7/20* | (2006.01) |

(52) U.S. Cl.
CPC ..... *G02B 27/0006* (2013.01); *G03F 7/70033* (2013.01); *G03F 7/70175* (2013.01); *G03F 7/70908* (2013.01); *G03F 7/70933* (2013.01); *H05G 2/003* (2013.01); *H05G 2/005* (2013.01); *H05G 2/008* (2013.01); *G01N 2223/204* (2013.01)

(58) Field of Classification Search
CPC .................................................. G02B 27/0006
USPC ...................................................... 250/358.1
See application file for complete search history.

(56) References Cited

U.S. PATENT DOCUMENTS

| | | | |
|---|---|---|---|
| 7,110,503 B1 | 9/2006 | Kumakhov | |
| 7,247,870 B2 | 7/2007 | Ershov et al. | |
| 7,655,925 B2 | 2/2010 | Bykanov et al. | |
| 2004/0109151 A1* | 6/2004 | Bakker et al. | 355/69 |
| 2006/0219959 A1* | 10/2006 | Hergenhan | G03F 7/70841 250/504 R |
| 2009/0090877 A1 | 4/2009 | Van Empel et al. | |
| 2009/0267005 A1 | 10/2009 | Bykanov et al. | |
| 2009/0272917 A1* | 11/2009 | Soer | G03F 7/70916 250/492.1 |
| 2010/0032590 A1 | 2/2010 | Bykanov et al. | |

(Continued)

*Primary Examiner* — Edwin Gunberg
(74) *Attorney, Agent, or Firm* — Suiter Swantz pc llo

(57) ABSTRACT

The present disclosure is directed to a system for protecting a reflective optic and/or any other surface in a plasma-based illumination system from debris by actively flowing gas against the debris flow direction. According to various embodiments, a vacuum chamber is configured to contain a target material, wherein a laser or discharge produced plasma is generated in response to an excitation of the target material. One or more outlets within the chamber are configured to receive gas flowing from a fluidically coupled gas source and further configured to actively flow the gas towards a source of debris and away from the reflective optic or any other protected surface at a controlled flow rate.

54 Claims, 13 Drawing Sheets

(56) References Cited

U.S. PATENT DOCUMENTS

2011/0170079 A1 7/2011 Bannie et al.
2012/0025109 A1* 2/2012 Abhari ................ G03F 7/70908
250/504 R

* cited by examiner

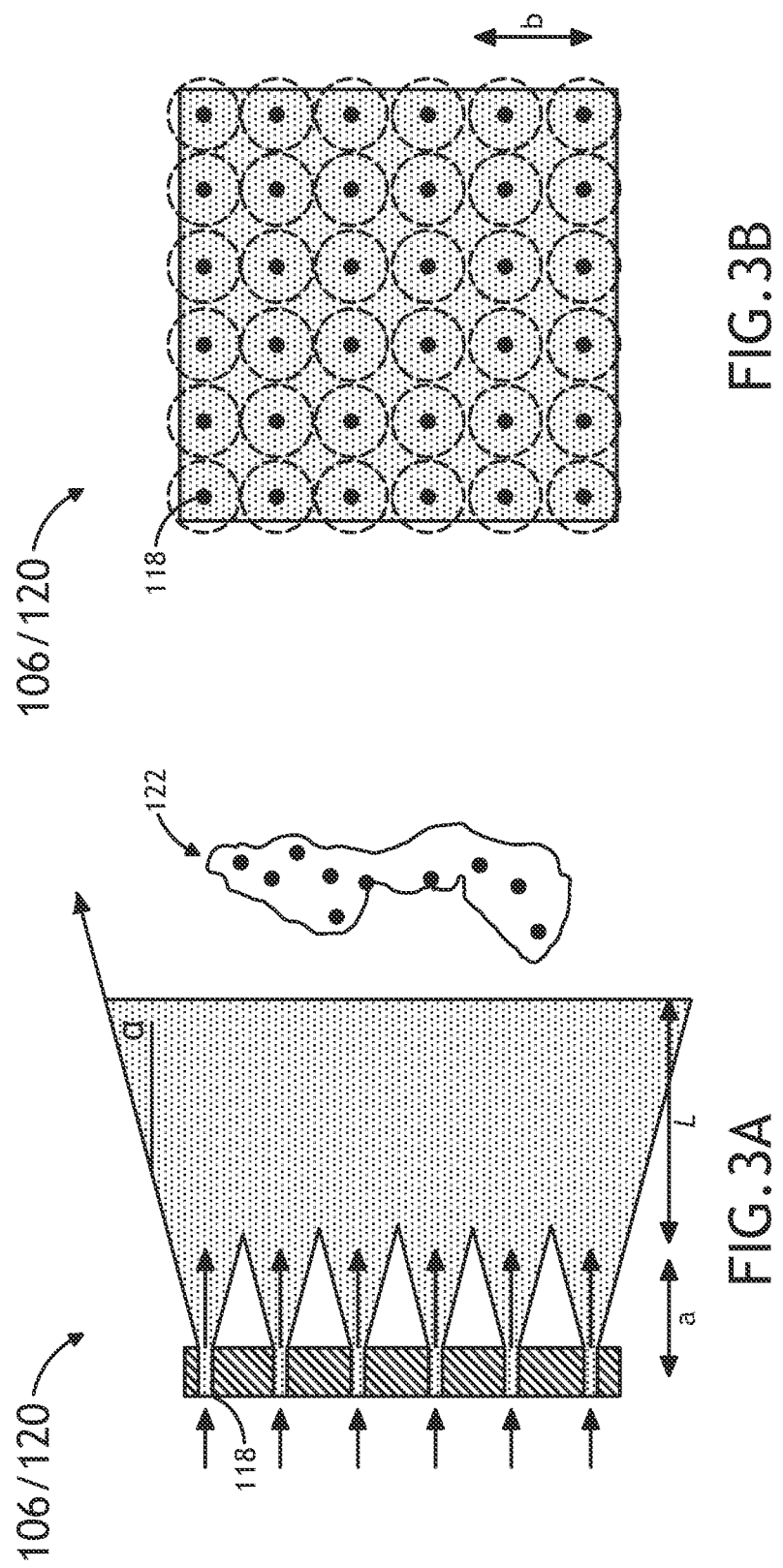

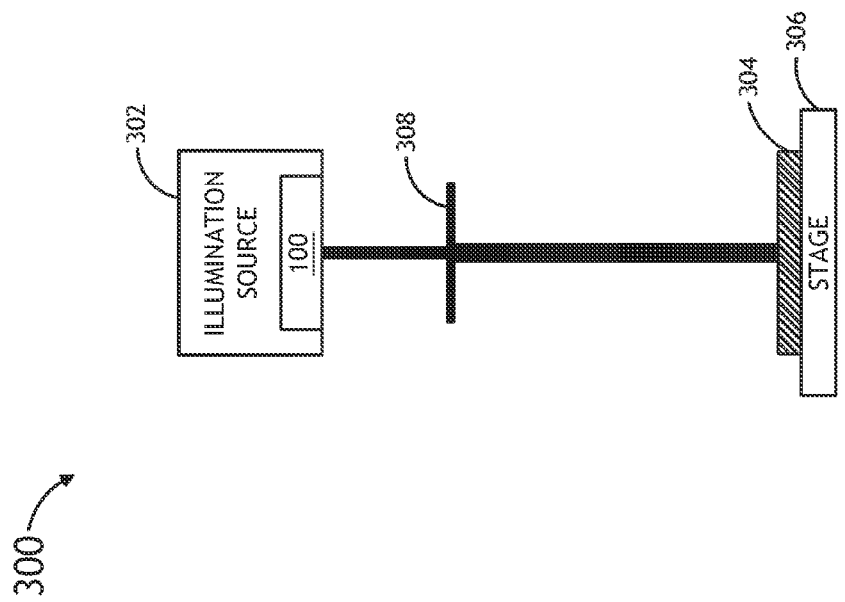

DEBRIS PROTECTION SYSTEM FOR REFLECTIVE OPTIC UTILIZING GAS FLOW

PRIORITY

The present application claims priority under 35 U.S.C. § 119(e) to U.S. Provisional Patent Application Ser. No. 61/810,265, entitled DEBRIS PROTECTION SYSTEM HAVING GAS FLOWING THROUGH REFLECTIVE OPTIC, By Alexey Kuritsyn et al., filed Apr. 10, 2013, or is an application of which currently co-pending application(s) are entitled to the benefit of the filing date. The above-referenced provisional patent application is hereby incorporated by reference in its entirety.

TECHNICAL FIELD

The present disclosure generally relates to the field of illumination systems and, more particularly, systems for preventing debris from reaching one or more surfaces in a plasma-based illumination system. For example, sources of debris which are accounted for may include, but are not limited to, atomic vapor, micro-particles, or other contaminants, which may be emitted from a target material, plasma site, plasma-facing components, eroded surfaces in proximity of the target material or the plasma, a target-forming structure, and/or any other structure within a plasma-based illumination system.

BACKGROUND

Plasma-based illumination systems, such as laser-produced plasma (LPP) sources, laser-sustained plasma (LSP) sources, laser-driven light sources (LDLS), or discharge-produced plasma (DPP) sources, are often used to generate soft x-ray, extreme ultraviolet (EUV), and vacuum ultraviolet (VUV) wavelengths of illumination (e.g. wavelengths around 120 nm or shorter) for applications such as defect inspection, photolithography, or metrology. The illumination may be emitted by a plasma that is generated at or near a site where target material (e.g. xenon, tin, or lithium) is deposited and irradiated by an excitation source, such as a laser. Illumination emanating from the plasma may be collected via a reflective optic, such as a collector mirror (e.g. a near-normal incidence or grazing incidence mirror), and then directed and/or focused along an illumination delivery path.

During operation of the plasma-based illumination system, debris such as atomic vapor, micro-particles, or contaminants (e.g. hydrocarbons or organics) may be emitted from various sources including, but not limited to, the target material, plasma site, plasma-facing components, eroded surfaces in proximity of the target material or the plasma, a target-forming structure, and/or any other structure within a plasma-based illumination system. These debris can sometimes reach the reflective optic and degrade its performance or cause irreparable damage. Some methods of protecting the reflective optic include deflection of debris by magnetic fields, utilization of debris vanes or shields consisting of thin foil separators to allow soft x-ray, EUV, or VUV light to go through but capturing the atomic condensable vapor, and circulating gas to generate a gas buffer between the target and the collector. Each of the foregoing methods has some drawbacks, as outlined below.

Coils producing magnetic fields have significant design complexity, are expensive, and work well only for deflecting ions, while not effective for stopping neutrals (and neutral particles), which are produced when ions undergo charge exchange with the buffer gas. Debris vanes lead to transmission light loss due to occlusion, require complicated alignment procedure, and any material that ends up condensing on the surface of the debris vanes can be a subject of secondary erosion or sputtering due to high energy ions produced by the source. A gas buffer region located between the target and the collector slows down high-energy ions and neutrals but is not as effective at suppressing diffusion of atomic vapor and micro-particles.

SUMMARY

This disclosure is directed to a system for actively flowing gas against the debris flow direction to provide greater protection against debris. Debris is prevented from reaching a reflective optic and/or any other protected surface, and the debris may be actively blown away from nearby surfaces as well. According to various embodiments, a vacuum chamber is configured to contain a target material, wherein a laser or discharge produced plasma is generated in response to an excitation of the target material. One or more outlets within the chamber are configured to receive gas flowing from a fluidically coupled gas source and further configured to actively flow the gas towards a source of debris and away from the reflective optic and/or any other protected surface at a controlled flow rate. For example, the one or more outlets may be configured to flow gas directly against debris such as, but not limited to, atomic vapor, micro-particles, or contaminants (e.g. hydrocarbons or organics) emitted from a target material, plasma site, plasma-facing components, eroded surfaces in proximity of the target material or the plasma, a target-forming structure, and/or any other structure within the vacuum chamber.

In some embodiments, the debris-mitigation system is incorporated into an illumination system, where the one or more outlets may include openings formed within or near a collector optic. For example, an illumination system may include a target material, an excitation source configured to irradiate the target material to generate a plasma, and a collector optic including a plurality of openings distributed across a reflective surface of the collector optic, the collector optic being configured to reflect illumination emanating from the plasma towards an illumination delivery path. A gas source may be fluidically coupled with the collector optic and may be configured to actively flow gas through the plurality of openings of the reflective surface of the collector optic towards a source of debris at a controlled flow rate. Additional/alternative embodiments are described below in the detailed description, and those skilled in the art will further appreciate that the embodiments or portions of the embodiments described herein may be combined or modified without departing from the scope of this disclosure.

In some embodiments, the illumination system (including the debris-mitigation system) is incorporated into an inspection system. In an embodiment, for example, an inspection system may include an illumination source configured to illuminate a sample, and a detector configured to receive illumination that is reflected, scatter, or radiated by the sample along an imaging path. The illumination source may include a target material, an excitation source configured to irradiate the target material to generate a plasma, a collector optic configured to reflect illumination emanating from the plasma towards an illumination delivery path, and one or more outlets configured to receive gas flowing from a fluidically coupled gas source, the one or more outlets being further configured to actively flow the gas towards a source of debris and away from a reflective surface of the collector optic at a controlled flow rate. A computing system in communication with the detector may be configured to locate or measure at least one defect of the sample based upon a signal associated with the detected illumination.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which:

FIG. 3A is a cross-sectional side view of a reflective optic or substantially transparent layer with openings for actively flowing gas towards a source of debris, in accordance with an embodiment of this disclosure;

FIG. 3B is a surface view of a reflective optic or substantially transparent layer with openings for actively flowing gas towards a source of debris, in accordance with an embodiment of this disclosure;

FIG. 11 is a block diagram illustrating a lithography system, in accordance with an embodiment of this disclosure.

DETAILED DESCRIPTION

Reference will now be made in detail to the subject matter disclosed, which is illustrated in the accompanying drawings.

Figure 1A:
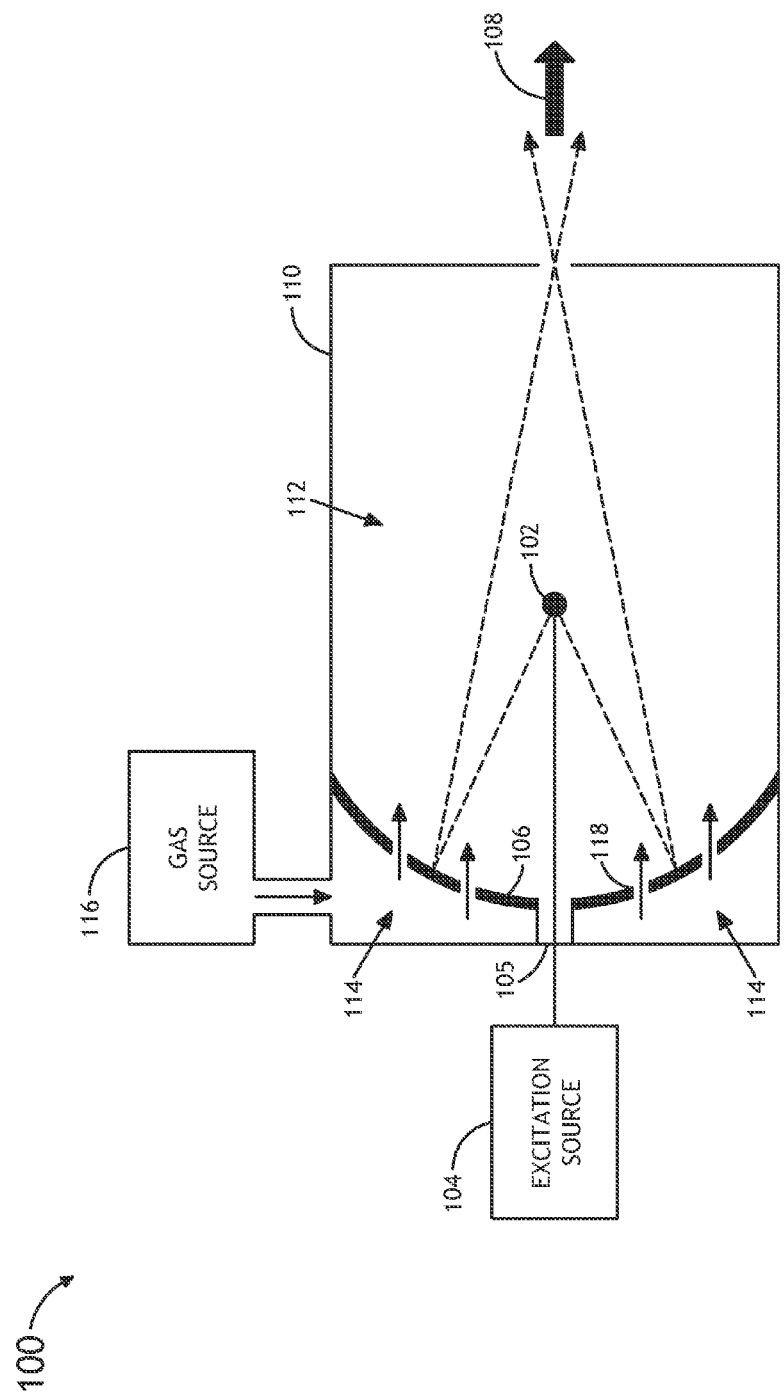
FIG. 1A is a block diagram illustrating an illumination system including a reflective optic having a plurality of openings for actively flowing gas towards a source of debris, in accordance with an embodiment of this disclosure.

FIGS. 1A through 11 generally illustrate a system for protecting a collector optic of a plasma-based illumination system from debris by actively flowing gas against the debris flow direction. As shown in FIGS. 1A and 1B, an illumination system 100, such as a laser-produced plasma soft x-ray, EUV, or VUV illumination source, may include an excitation source 104, such as a laser, configured to irradiate a target material 102. Alternatively, in a discharge-produced plasma source (not shown), the excitation source may include, but is not limited to, coils configured to magnetically excite the target material. In an embodiment, the excitation source 104 is configured to irradiate the target material 102 with a beam of illumination or a train of light pulses delivered into a cavity 112 defined by a vacuum chamber 110 and a reflective surface of a collector optic 106. As shown in FIGS. 1A and 1B, the illumination emanating from the excitation source 104 may be directed through a laser window 105 of the vacuum chamber 110. Suitable laser devices for the excitation source 104, among other components of the illumination system 100, are described in U.S. Patent Application Publication No. 2010/0032590 and U.S. Pat. Nos. 7,247,870 and 7,655,925, which are entirely incorporated herein including any sources of literature referenced therein.

Figure 1B:
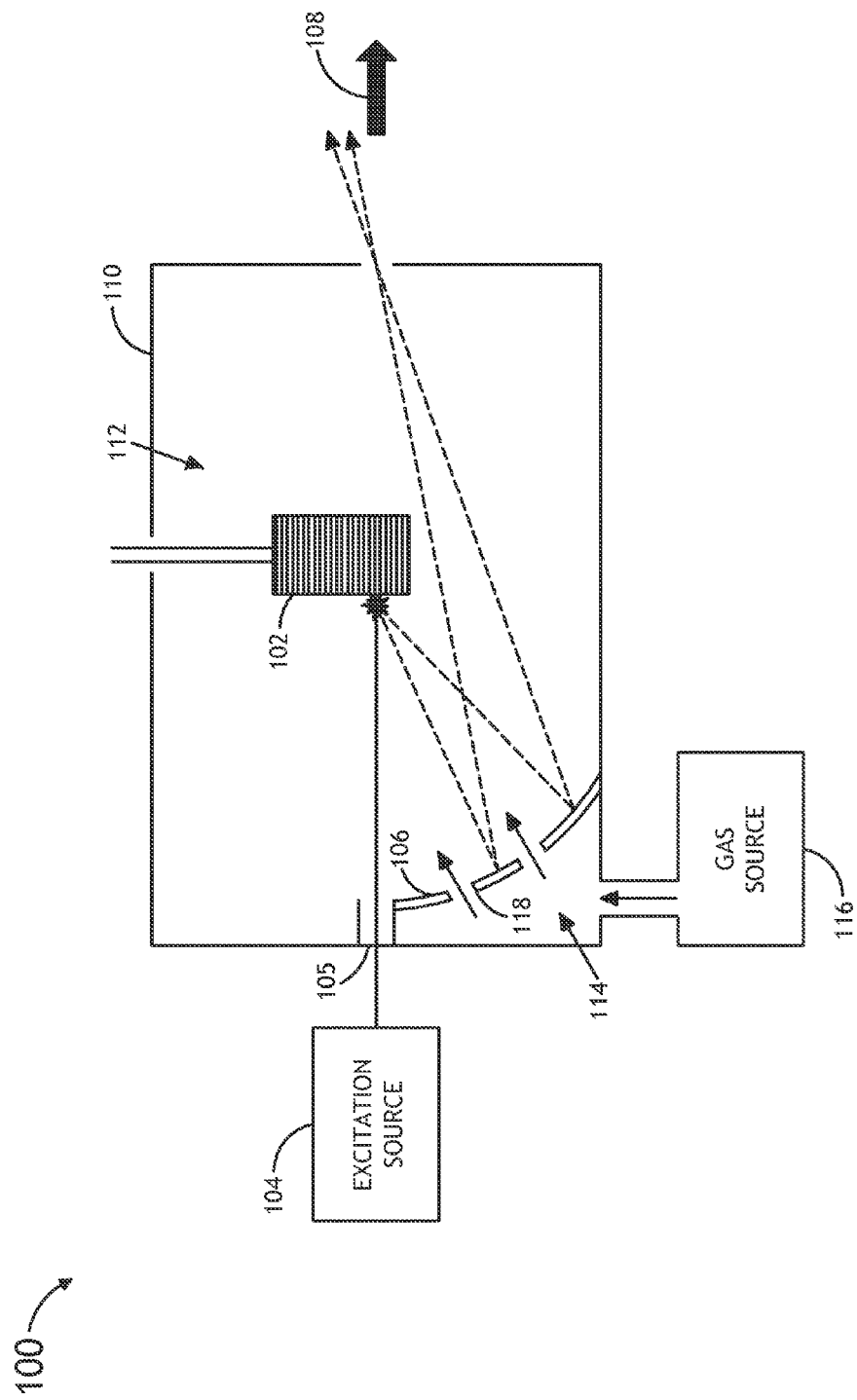
FIG. 1B is a block diagram illustrating an illumination system including a reflective optic having a plurality of openings for actively flowing gas towards a source of debris, in accordance with an embodiment of this disclosure.

In some embodiments, the target material 102 is deposited via a target material delivery system, which may be configured to deliver droplets of the target material 102 into the cavity 112 to an irradiation region where the droplets will interact with illumination from the excitation source 104 to ultimately produce a plasma and generate a soft x-ray, EUV, or VUV emission. The target material 102 may include, but is not necessarily limited to, a material that includes tin, lithium, xenon or combinations thereof. In some embodiments, the target material 102 is delivered in the form of liquid droplets, solid pellets, and/or solid particles contained within liquid droplets. Alternative targets or target-forming structures may be utilized, such as a drum 102, which may be cooled cryogenically, or utilizing a cold finger. In an embodiment, the cooled drum 102 may be coated with xenon ice, as illustrated in FIG. 1B. Those skilled in the art will appreciate that various target materials and deposition techniques may be used without departing from the scope of this disclosure.

As shown in FIG. 1A, the collector optic 106 may include an aperture configured to allow illumination from the excitation source 104 to pass through and reach the target material 102 deposited within the irradiation region of the cavity 112. Alternatively, as shown in FIG. 1B, the collector optic 106 may be located off-axis from the irradiation path. The collector optic 106 may be configured to receive soft x-ray, EUV, or VUV emissions from the resulting plasma and directionally reflect the soft x-ray, EUV, or VUV illumination towards an intermediate focal region to an illumination delivery path 108. The collector optic 106 may include a grazing-incidence mirror or a near-normal incidence collector mirror having a reflective surface in the form of a prolate spheroid (i.e., an ellipse rotated about its major axis), which may include a graded multi-layer coating with alternating layers of molybdenum and silicon, and in some cases one or more high temperature diffusion barrier layers, smoothing layers, capping layers and/or etch stop layers. In some embodiments, the reflective surface of the collector optic has a surface area in the range of approximately 100 and 10,000 cm$^2$ and may be disposed approximately 0.1 to 2.5 meters from the target material 102 or irradiation region. Those skilled in the art will appreciate that the foregoing ranges are exemplary and that various optics may be used in place of, or in addition to, the prolate spheroid mirror for collecting and directing light to an intermediate location for subsequent delivery to a device utilizing soft x-ray, EUV, or VUV illumination, such as an inspection system or a photolithography system.

In some embodiments, the illumination system 100 may further include an emissions controller, which may also include a firing control system for triggering one or more lamps and/or laser devices in the excitation source 104 to generate pulses of illumination for delivery into the cavity 112. The illumination system 100 may further include a droplet position detection system which may include one or more droplet imagers and/or light curtains configured to indicate the position and/or timing of one or more droplets (e.g. relative to the irradiation region). A droplet position detection feedback system may be configured to receive an output from the droplet images and further configured to compute a droplet position and trajectory, from which a droplet error can be computed (e.g. on a droplet-by-droplet basis or based on an average). The droplet error may then be provided as an input to an excitation source controller, which may be configured to provide a position, direction, and/or timing correction signal to the excitation source 104 to control a source timing circuit and/or to control a beam position and shaping system. Accordingly, the trajectory and/or focal power of the illumination beam or pulses being delivered to the irradiation region of the cavity 112 may be dynamically adjusted according to the droplet position and/or trajectory associated with the target material 102.

As shown in FIGS. 1A and 1B, and further illustrated in FIGS. 2 through 9 according to various embodiments of the disclosure, the illumination system 100 may include a debris-mitigation system for preventing debris, such as, but not limited to, atomic vapor, micro-particles, or contaminants (e.g. hydrocarbons or organics) emitted from a target material, plasma site, plasma-facing components, eroded surfaces in proximity of the target material or the plasma, target-forming structures (e.g. cryogenically cooled drum), or any other structure from reaching a reflective optic of the illumination system, such as the collector optic 106, or any other protected surface such as, but not limited to, a laser window 105, a vacuum chamber window, a reflective optic or an optical filter of a tool (e.g. diagnostic tool) positioned within or relative to the illumination system 100. The debris mitigation system may include one or more outlets 118 configured to actively flow gas from a fluidically coupled gas source 116 towards the source of debris and away from the reflective optic 106. The actively flown gas may further establish a buffer in proximity of the reflective optic 106, which may slow down high-energy ions and/or neutrals, thereby preventing them from eroding the reflective optic 106.

According to various embodiments, the gas may include a gas or a mixture of gases such as, but not limited to, hydrogen, helium, nitrogen, argon, or a combination thereof. In some embodiments, the selected gas or mixture of gases has higher EUV transmission characteristics than the target material (e.g. higher EUV transmission than xenon) to improve EUV transmission of the system by blowing away or diluting the lower transmission target material in addition to deflecting at least a portion of the debris.

The gas source 116 may include a gas manifold or any other container suitable for holding the selected gas or mixture of gases. The gas source 116 may further include a flow controller, such as an analog and/or digital adjustment interface, configured for manual or programmable adjustment of the flow rate. A suitable flow rate for deflecting debris may be, for example, in the range of approximately 0.5 to 20 standard liters per minute (slm). The gas source 116 may be configured to deliver gas at a predetermined or user/program adjusted flow rate to the one or more outlets 118 via at least one cavity, lumen, or any other structure or combination of structures defining one or more independent or shared gas flow pathways.

Figure 2:
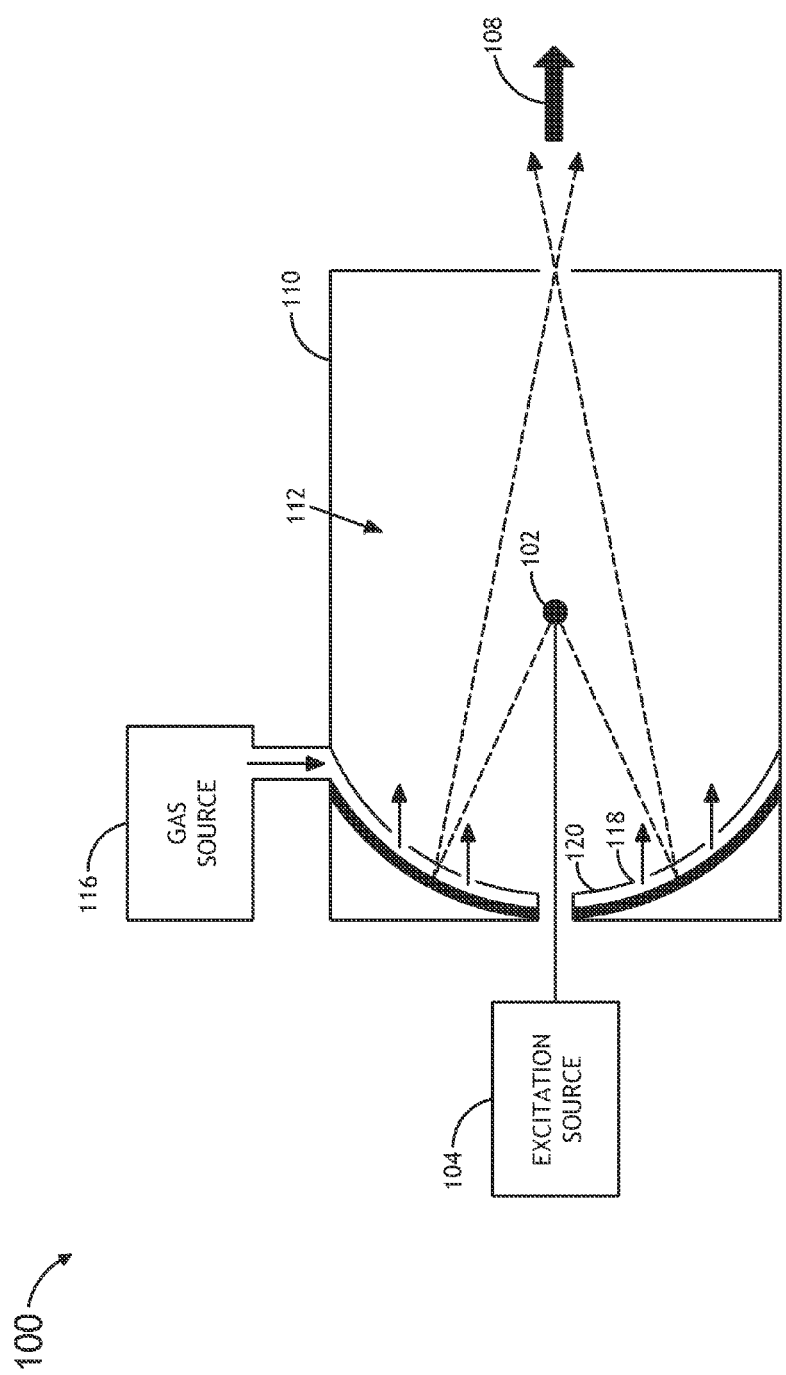
FIG. 2 is a block diagram illustrating an illumination system including a substantially transparent layer adjacent to a reflective optic, the substantially transparent layer having a plurality of openings for actively flowing gas towards a source of debris, in accordance with an embodiment of this disclosure.

In some embodiments (as shown in FIGS. 1A and 1B), the outlets 118 may include a plurality of openings formed in the reflective optic 106. For example, the gas may be actively flown through a plurality of uniformly or non-uniformly distributed openings 118 spanning at least a portion of the reflective optic 106. Alternatively, as shown in FIG. 2, the openings 118 may be formed in a substantially transparent layer 120 adjacent to the reflective optic 106. FIGS. 3A and 3B conceptually illustrate gas flow through the openings 118 of the reflective optic 106 or, in some embodiments, through the openings 118 of a substantially transparent layer 120 adjacent to the reflective optic 106.

Figure 3C:
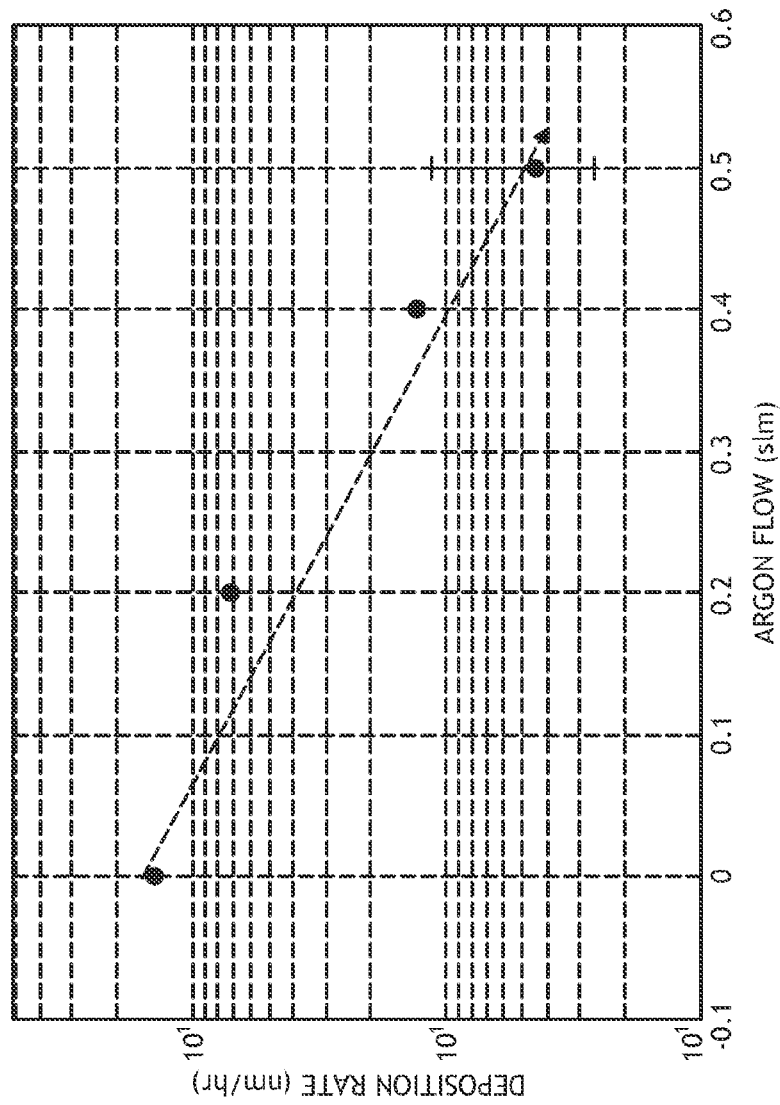
FIG. 3C is a data plot of debris deposition on a reflective optic relative to gas flow rate, in accordance with an embodiment of this disclosure.

In the case of atomic vapor, effectiveness of the protection of the reflective optic 106 or any other protected surface from the deposition of atomic vapor 122 can be estimated by calculating dimensionless Peclet number defined as the ratio of advection of the vapor by the flow to the rate of diffusion Pe=vL/D, where v is the gas flow, L is the characteristic length and D is the diffusion coefficient of vapor material in the gas. Then, the vapor attenuation factor is equal to $e^{(-Pe)}$. Depending on desired degree of vapor attenuation, it is possible to determine the gas flow required to achieve this Peclet number for particular operational conditions. For example, Peclet number Pe>4, would provide >50× vapor attenuation. Then, assuming, for example, that argon gas is flown through the collector of 600 cm$^2$ area, the flow uniformly expands at an angle (e.g. α=45°) after passing through the collector and reaches average pressure (e.g. 30 mTorr), which occupies the length (e.g. L=10 cm). Taking, for example, Aluminum atomic vapor at room temperature diffusing against the argon flow, it is possible to estimate that argon flow required to achieve P=4 is approximately 5 slm. FIG. 3C is a data plot showing experimental results obtained by the inventors by flowing Argon relative to a surface. As can be seen, the deposition rate significantly decreases in response to the flow rate.

The gas flow protection scheme illustrated in FIGS. 1A though 3B may become more effective as expanding gas cones from adjacent openings 118 overlap. The overlap occurs at a distance a from the reflective optic 106 (or the substantially transparent layer 120), which is of the order of spacing b between the openings 118. Thus, the spacing b between the openings 118 may be selected so that distance a is much less than the distance from the reflective optic 106 to the target material 102 or the irradiation region. At the same time, the total surface area occupied by the openings 118 should be much less than the surface area of the reflective surface of the reflective optic 106 to avoid degradation of total reflectivity. The reflective optic 106 may also be located at a distance greater than the characteristic length L from the soft x-ray, EUV, or VUV emission area. To maintain reflectivity of the reflective optic 106, the openings 118 may be distributed with a spacing between one another that is at least five times smaller than a distance between the reflective optic 106 and the target material 102 or the irradiation region, and the total surface area occupied by the openings 118 may be at least 10 times smaller than the surface area of the reflective optic 106. It is noted, however, that the foregoing parameters are exemplary and should not be construed as restrictions on the present disclosure.

Figure 4:
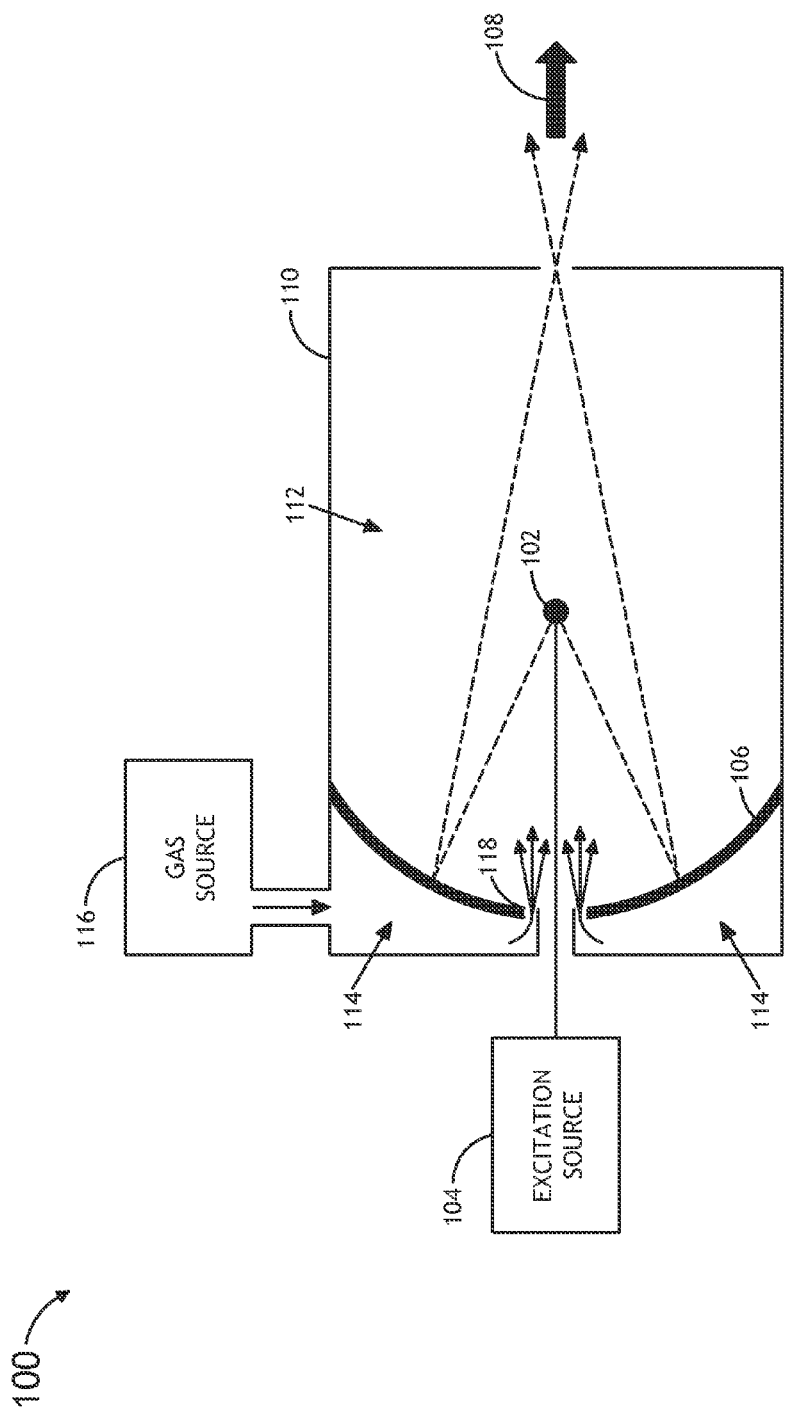
FIG. 4 is a block diagram illustrating an illumination system with at least one opening formed along an inner edge of a reflective optic for actively flowing gas towards a source of debris, in accordance with an embodiment of this disclosure.
Figure 5:
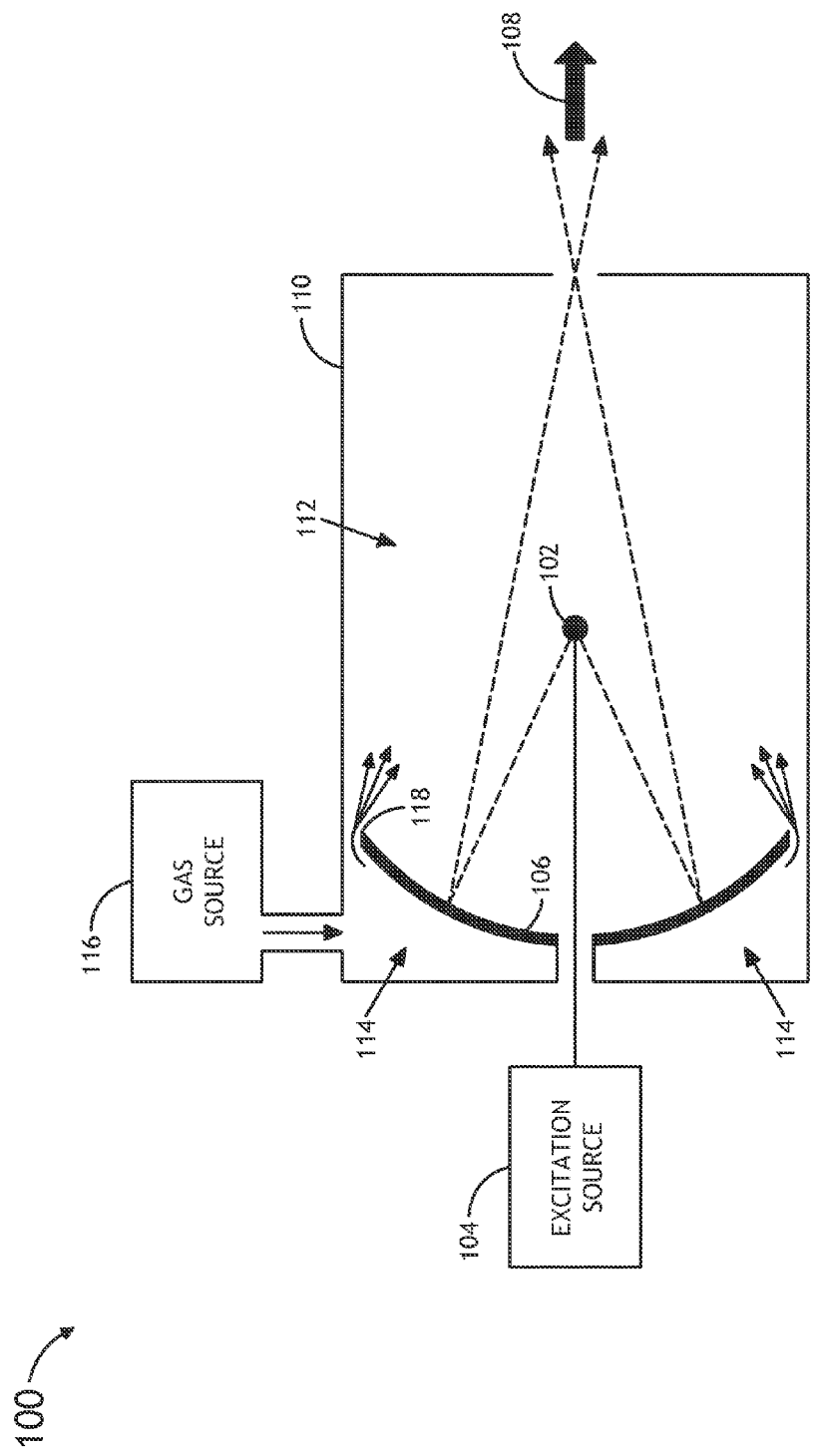
FIG. 5 is a block diagram illustrating an illumination system with at least one opening formed along an outer edge of a reflective optic for actively flowing gas towards a source of debris, in accordance with an embodiment of this disclosure.

FIGS. 4 and 5 illustrate embodiments of the debris-mitigation system where gas is alternatively or additionally flown through one or more openings 118 located near or formed along an inner edge of the reflective optic 106 (FIG. 4) and/or an outer edge of the reflective optic 106 (FIG. 5). In all of the foregoing embodiments and any combination thereof, the openings 118 may be oriented to allow for directional gas flow towards the source of debris or towards multiple sources of debris (i.e. against the debris path or paths). In the embodiments illustrated in FIGS. 4 and 5, the illumination system 100 may include a greater distance between the reflective optic 106 and the target material 102 or irradiation region to enable sufficient dispersion of the gas so that portions of the reflective optic 106 that are distant from the openings 118 are protected when the gas fed in through the one or more openings 118 expands. In some embodiments, several openings 118 are distributed along the inner edge and/or outer edge of the reflective optic 106. Alternatively, the one or more openings 118 may include an annular opening or one or more partial annuluses (e.g. semi-circular opening) formed along the inner edge and/or outer edge of the reflective optic 106.

Figure 6:
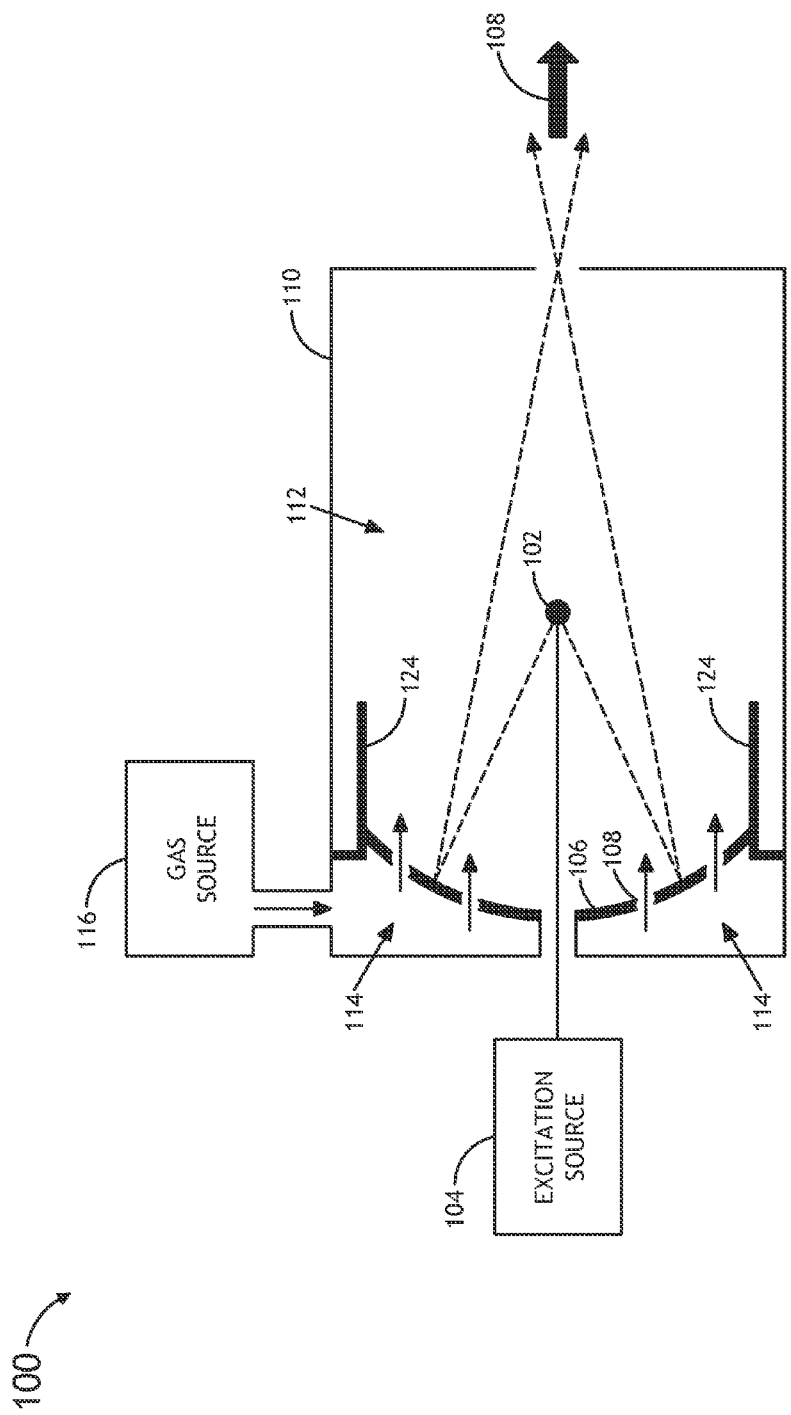
FIG. 6 is a block diagram illustrating an illumination system including a reflective optic having a plurality of openings for actively flowing gas towards a source of debris, wherein the illumination system further includes a tubular structure bounding an outer edge of the reflective optic, in accordance with an embodiment of this disclosure.
Figure 7:
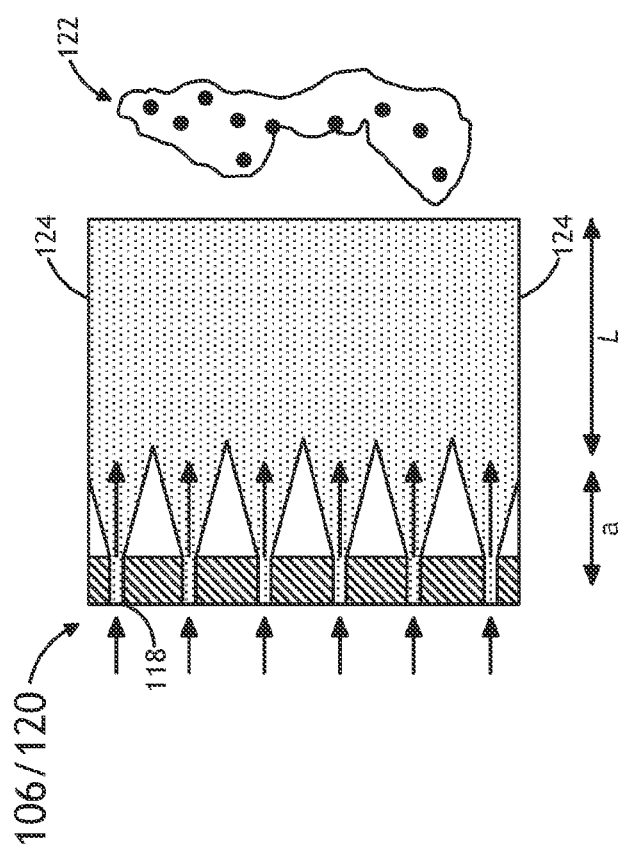
FIG. 7 is a cross-sectional side view of a reflective optic or substantially transparent layer with openings for actively flowing gas towards a source of debris, wherein an outer edge of the reflective optic or substantially transparent layer is bounded by a tubular structure, in accordance with an embodiment of this disclosure.

As shown in FIGS. 6 and 7, the debris-mitigation system may further include a tubular structure 124 bounding the outer edge of the reflective optic 106 to reduce flow expansion (e.g. prevent gas from expanding outwards beyond the outer edge of the reflective optic 106, as shown in FIG. 7), where the tubular structure 124 may be dimensioned and arranged so that it does not block the incoming or outgoing illumination path. The reduced expansion may advantageously reduce the flow rate necessary to deflect the debris 122. For example, repeating the estimates provided above with similar illustrative parameters for the case of non-expanding argon flow, the required gas flow rate for similar effectiveness of debris-mitigation is approximately 2.8 slm. This is comparatively less than the required flow rate of approximately 5 slm when gas expansion is taken into account. In some embodiments, the tubular structure 124 may include or may be coupled to a cooling element or a cooling system (e.g. a cryogenic panel or anti-freeze coolant path) enabling the inner-facing surface of the tubular structure 124 to be cooled so that radially diffusing vapor is trapped (i.e. sticks to the inner-facing structure of the tubular structure 124) before it can reach the reflective optic 106.

Figure 8:
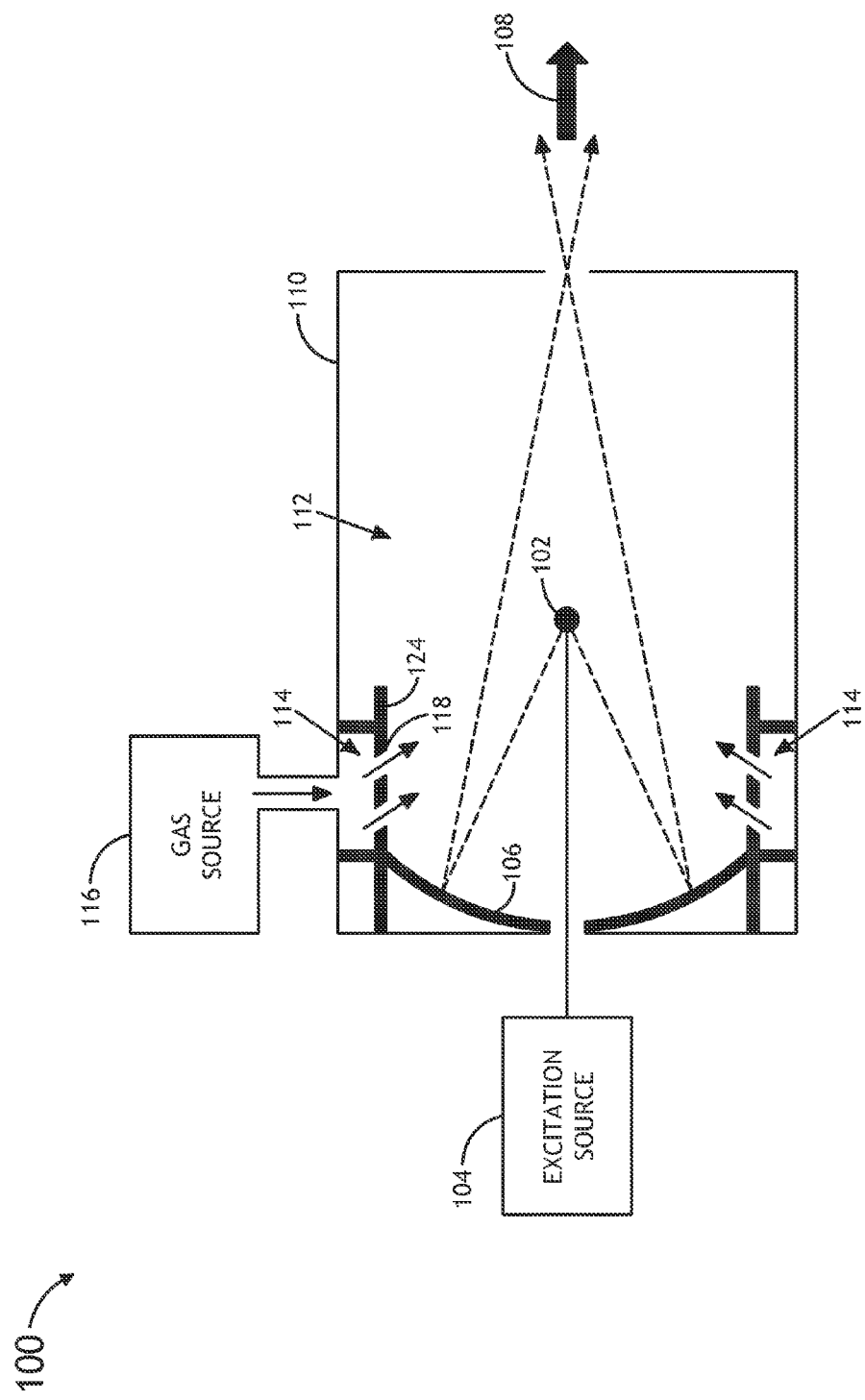
FIG. 8 is a block diagram illustrating an illumination system including a reflective optic bounded by a tubular structure, the tubular structure having a plurality of openings for actively flowing gas towards a source of debris, in accordance with an embodiment of this disclosure.
Figure 9:
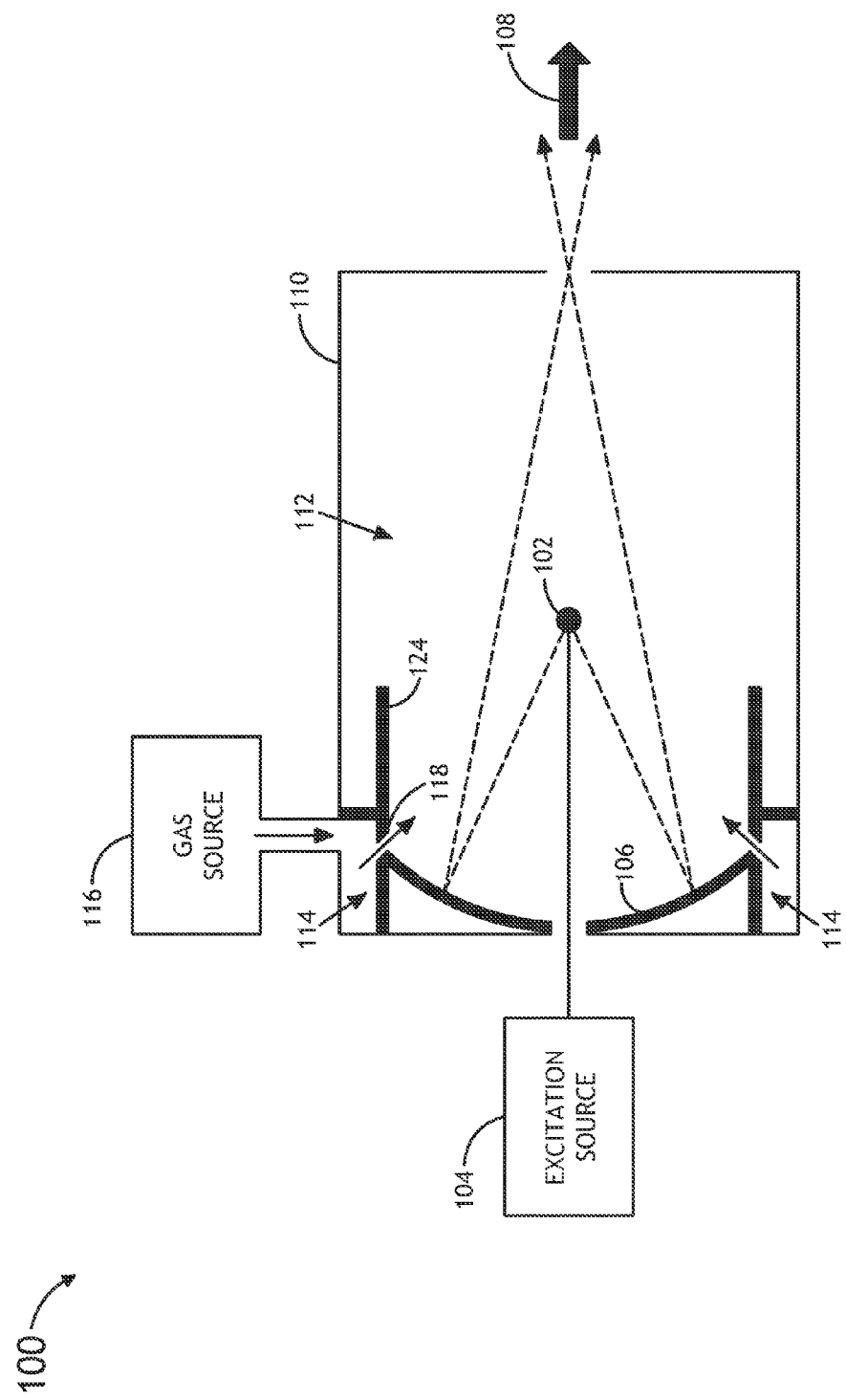
FIG. 9 is a block diagram illustrating an illumination system including a reflective optic bounded by a tubular structure with at least one opening formed along an inner edge of the tubular structure for actively flowing gas towards a source of debris, in accordance with an embodiment of this disclosure.

While FIG. 6 illustrates an embodiment of the illumination system 100 where the tubular structure 124 is included in a debris-mitigation system similar to the embodiment shown in FIG. 1, those skilled in the art will appreciate that any of the embodiments illustrated in FIGS. 1 through 5 may include a tubular structure 124 bounding the outer edge of the reflective optic 106 (or the outer edge of a substantially transparent layer 120 adjacent to the reflective optic 106). Further, as shown in FIGS. 8 and 9, the one or more gas flow outlets 118 may include a plurality of openings 118 formed within the tubular structure (FIG. 8) or at least one annular opening 118 or partial annulus formed along an inner edge of tubular structure 124 (FIG. 9).

Figure 10:
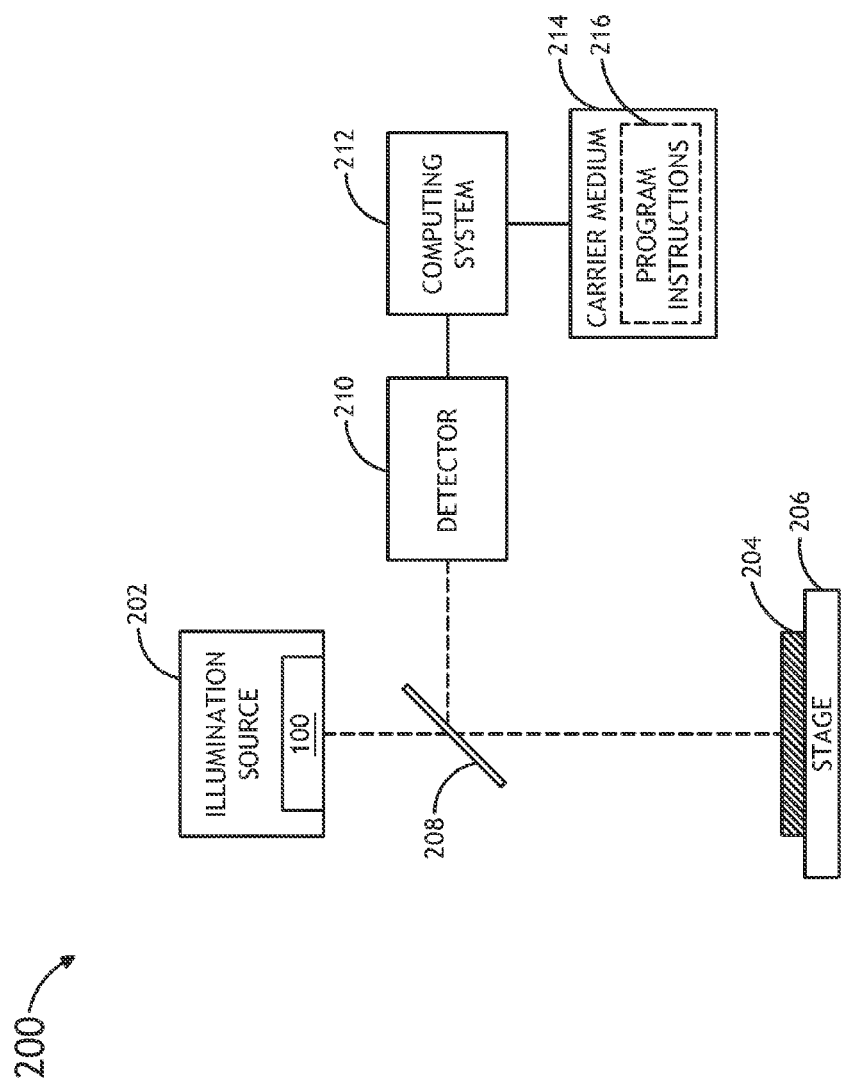
FIG. 10 is a block diagram illustrating an inspection system, in accordance with an embodiment of this disclosure.

Soft x-ray, EUV, VUV or any other band of plasma-generated illumination may be used for semiconductor process applications, such as inspection, photolithography, or metrology. For example, as shown in FIG. 10, an inspection system 200 may include an illumination system 202 incorporating an illumination system, such as the illumination system 100 described above. The inspection system 200 may further include a stage 206 configured to support at least one sample 204, such as a semiconductor wafer or a mask. The illumination source 200 may be configured to illuminate the sample 204 via an illumination path, and illumination that is reflected, scattered, or radiated from the sample 204 may be directed along an imaging path to at least one detector 210 (e.g. camera or array of photo-sensors), wherein the illumination and imaging paths may be delineated by one or more optical elements (e.g. beam splitter 208). A computing system 212 that is communicatively coupled to the detector 210 may be configured to process signals associated with the detected illumination signals to locate and/or measure various attributes of one or more defects of the sample 204 according to an inspection algorithms embedded in program instructions 216 executable by a processor of the computing system 212 from a non-transitory carrier medium 214.

For further example, FIG. 11 generally illustrates a photolithography system 300 including an illumination source 302 incorporating the illumination system 100 described above. The photolithography system may include stage 306 configured to support at least one substrate 304, such as a semiconductor wafer, for lithography processing. The illumination source 302 may be configured to perform photolithography upon the substrate 304 or a layer disposed upon the substrate 304 with illumination transferred by the illumination system 100 along the illumination delivery path 108 to an output of the illumination source 302. For example, the output illumination may be directed through a reticle 308 to the substrate 304 to pattern the surface of the substrate 304 or a layer on the substrate 304 according an illuminated reticle pattern. The exemplary embodiments illustrated in FIGS. 10 and 11 are generally depict applications of the debris-mitigated illumination system 100 described above; however, those skilled in the art will appreciate that the system 100 can be applied in a variety of contexts without departing from the scope of this disclosure.

Those having skill in the art will further appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. In some embodiments, various steps, functions, and/or operations are carried out by one or more of the following: electronic circuits, logic gates, multiplexers, programmable logic devices, ASICs, analog or digital controls/switches, microcontrollers, or computing systems. A computing system may include, but is not limited to, a personal computing system, mainframe computing system, workstation, image computer, parallel processor, or any other device known in the art. In general, the term "computing system" is broadly defined to encompass any device having one or more processors, which execute instructions from a carrier medium. Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A system, comprising:
   an unsegmented reflective optic;
   a vacuum chamber configured to contain a target material, wherein a plasma is generated in response to an excitation of the target material, and wherein the unsegmented reflective optic includes a reflective surface configured to receive illumination emitted by the plasma;
   two or more outlets, the two or more outlets configured to receive gas flowing from a fluidically coupled gas source, the two or more outlets being further configured to actively flow the gas towards a source of debris and away from the reflective surface of the unsegmented reflective optic at a controlled flow rate, wherein the two or more outlets are configured to flow the gas through two or more openings formed in the reflective surface of the unsegmented reflective optic, wherein the two or more openings are configured to provide two or more expanding streams of the gas flowing away from the reflective surface of the unsegmented reflective optic, wherein the two or more openings are distributed across the reflective surface such that at least two expanding streams of the gas of the two or more expanding streams of the gas overlap; and
   a tubular structure bounding an outer edge of the unsegmented reflective optic, the tubular structure being configured to prevent the gas from expanding outwards beyond the outer edge of the unsegmented reflective optic.

2. The system of claim 1, wherein the unsegmented reflective optic has a surface area in the range of approximately 100 to 10,000 $cm^2$.

3. The system of claim 1, wherein the unsegmented reflective optic is disposed approximately 0.1 to 2.5 meters from the target material.

4. The system of claim 1, wherein the two or more openings are distributed with a spacing between one another that is at least five times smaller than a distance between the unsegmented reflective optic and the target material.

5. The system of claim 1, wherein an area occupied by the two or more openings is at least 10 times smaller than a surface area of the unsegmented reflective optic.

6. The system of claim 1, wherein the target material includes xenon, lithium, or tin.

7. The system of claim 1, wherein the target material includes xenon, and wherein the gas comprises a gas or a mixture of gases having a higher EUV transmission characteristic than the target material.

8. The system of claim 1, wherein the gas includes at least one of hydrogen, helium, nitrogen, and argon.

9. The system of claim 1, wherein the controlled flow rate of the gas is in the range of approximately 0.5 to 20 standard liters per minute.

10. The system of claim 1, wherein the reflective surface comprises:
    a substantially transparent layer disposed adjacent to a reflective layer, wherein the two or more outlets are configured to flow the gas through two or more openings formed in the substantially transparent layer.

11. The system of claim 1, wherein the two or more outlets include an opening formed along an outer edge of the unsegmented reflective optic.

12. The system of claim 1, wherein the two or more outlets include an opening formed along an inner edge of the unsegmented reflective optic.

13. The system of claim 1, wherein the two or more outlets include two or more openings formed within the tubular structure.

14. The system of claim 1, wherein the two or more outlets include an opening formed along an inner edge of the tubular structure.

15. The system of claim 1, wherein the tubular structure is cooled and is configured to trap diffused vapor, thereby preventing the diffused vapor from reaching the unsegmented reflective optic.

16. The system of claim 1, wherein the source of debris includes one or more of: the target material, the plasma, a plasma-facing component, an eroding surface in proximity of the target material or the plasma, or a target-forming structure.

17. The system of claim 1, wherein the debris includes one or more of: atomic vapor, micro-particles, or contaminants.

18. The system of claim 1, wherein the illumination comprises soft x-ray, EUV, or VUV illumination.

19. An illumination system, comprising:
    a target material;
    an excitation source configured to irradiate the target material to generate a plasma;
    an unsegmented collector optic including two or more openings formed in a reflective surface of the collector optic, the collector optic being configured to reflect illumination emanating from the plasma towards an illumination delivery path;
    a gas source configured to actively flow gas through the two or more openings formed in the reflective surface of the unsegmented collector optic towards a source of debris at a controlled flow rate and away from the reflective surface of the unsegmented collector optic, wherein the two or more openings are configured to provide two or more expanding streams of the gas flowing away from the reflective surface of the unsegmented reflective optic, wherein the two or more openings are distributed across the reflective surface such that at least two expanding streams of the gas of the two or more expanding streams of the gas overlap; and a tubular structure bounding an outer edge of the reflective surface of the unsegmented collector optic, the tubular structure being configured to prevent the gas from expanding outwards beyond the outer edge of the reflective surface of the unsegmented collector optic.

20. The illumination system of claim 19, wherein the reflective surface of the unsegmented collector optic has a surface area in the range of approximately 100 to 10,000 cm$^2$.

21. The illumination system of claim 19, wherein the reflective surface of the collector optic is disposed approximately 0.1 to 2.5 meters from the target material.

22. The illumination system of claim 19, wherein the two or more openings are distributed with a spacing between one another that is at least five times smaller than a distance between the reflective surface of the unsegmented collector optic and the target material.

23. The illumination system of claim 19, wherein an area occupied by the two or more openings is at least 10 times smaller than a surface area of the reflective surface of the unsegmented collector optic.

24. The illumination system of claim 19, wherein the target material includes xenon, lithium, or tin.

25. The illumination system of claim 19, wherein the target material includes xenon, and wherein the gas comprises a gas or a mixture of gases having a higher EUV transmission characteristic than the target material.

26. The illumination system of claim 19, wherein the gas includes at least one of hydrogen, helium, nitrogen, and argon.

27. The illumination system of claim 19, wherein the controlled flow rate of the gas is in the range of approximately 0.5 to 20 standard liters per minute.

28. The illumination system of claim 19, wherein the tubular structure is cooled and is configured to trap diffused vapor, thereby preventing the diffused vapor from reaching the reflective surface of the unsegmented collector optic.

29. The illumination system of claim 19, wherein the source of debris includes one or more of: the target material, the plasma, a plasma-facing component, an eroding surface in proximity of the target material or the plasma, or a target-forming structure.

30. The illumination system of claim 19, wherein the debris includes one or more of: atomic vapor, micro-particles, or contaminants.

31. The illumination system of claim 19, wherein the illumination comprises soft x-ray, EUV, or VUV illumination.

32. An inspection system, comprising:
a stage configured to support a sample;
an illumination source configured to illuminate a sample, the illumination source including a target material, an excitation source configured to irradiate the target material to generate a plasma, an unsegmented collector optic configured to reflect illumination emanating from the plasma towards an illumination delivery path, and two or more outlets configured to receive gas flowing from a fluidically coupled gas source, the two or more outlets being further configured to actively flow the towards a source of debris and away from a reflective surface of the unsegmented collector optic at a controlled flow rate, wherein the two or more outlets are configured to flow the gas through two or more openings formed in the reflective surface, wherein the two or more openings are configured to provide two or more expanding streams of the gas flowing away from the reflective surface, wherein the two or more openings are distributed across the reflective surface such that at least two expanding streams of the gas of the two or more expanding streams of the gas overlap;

a tubular structure bounding an outer edge of the unsegmented collector optic, the tubular structure being configured to prevent the gas from expanding outwards beyond the outer edge of the unsegmented collector optic:

a detector configured to receive illumination that is reflected, scattered, or radiated by the sample along an imaging path; and a computing system in communication with the detector, the computing system being configured to locate or measure at least one defect of the sample based upon a signal associated with the detected illumination.

33. The inspection system of claim 32, wherein the reflective surface comprises:
a substantially transparent layer disposed adjacent to a reflective layer, wherein the two or more outlets are configured to flow the gas through two or more openings formed in the substantially transparent layer.

34. The inspection system of claim 32, wherein the two or more outlets include an opening formed along an outer edge of the reflective surface of the unsegmented collector optic.

35. The inspection system of claim 32, wherein the two or more outlets include an opening formed along an inner edge of the reflective surface of the unsegmented collector optic.

36. The inspection system of claim 32, wherein the two or more outlets include two or more openings formed within the tubular structure.

37. The inspection system of claim 32, wherein the two or more outlets include an opening formed along an inner edge of the tubular structure.

38. The inspection system of claim 32, wherein the tubular structure is cooled and is configured to trap diffused vapor, thereby preventing the diffused vapor from reaching the reflective surface of the unsegmented collector optic.

39. The inspection system of claim 32, wherein the source of debris includes one or more of: the target material, the plasma, a plasma-facing component, an eroding surface in proximity of the target material or the plasma, or a target-forming structure.

40. The inspection system of claim 32, wherein the debris includes one or more of: atomic vapor, micro-particles, or contaminants.

41. The inspection system of claim 32, wherein the illumination comprises soft x-ray, EUV, or VUV illumination.

42. A system, comprising:
a vacuum chamber configured to contain a target material, wherein a plasma is generated in response to an excitation of the target material; and
two or more outlets configured to receive gas flowing from a fluidically coupled gas source, the two or more outlets being further configured to actively flow the gas towards a source of debris and away from an unsegmented surface at a controlled flow rate, wherein the two or more outlets are configured to flow the gas through two or more openings formed in the unsegmented surface, wherein the two or more openings are configured to provide two or more expanding streams of the gas flowing away from the reflective surface of the unsegmented surface, wherein the two or more openings are distributed across the unsegmented surface such that at least two expanding streams of the gas of the two or more expanding streams of the gas overlap, wherein an outer edge of the unsegmented surface is bounded by a tubular structure configured to prevent the gas from expanding outwards beyond the outer edge of the unsegmented surface.

43. The system of claim 42, wherein the unsegmented surface comprises:
a substantially transparent layer disposed adjacent to a surface layer, wherein the two or more outlets are configured to flow the gas through two or more openings formed in the substantially transparent layer.

44. The system of claim 42, wherein the two or more outlets include an opening formed along an outer edge of the surface.

45. The system of claim 42, wherein the two or more outlets include an opening formed along an inner edge of the surface.

46. The system of claim 42, wherein the two or more outlets include two or more openings formed within the tubular structure.

47. The system of claim 42, wherein the two or more outlets include an opening formed along an inner edge of the tubular structure.

48. The system of claim 42, wherein the tubular structure is cooled and is configured to trap diffused vapor, thereby preventing the diffused vapor from reaching the surface.

49. The system of claim 42, wherein the source of debris includes one or more of: the target material, the plasma, a plasma-facing component, an eroding surface in proximity of the target material or the plasma, or a target-form ing structure.

50. The system of claim 42, wherein the debris includes one or more of: atomic vapor, micro-particles, or contaminants.

51. The system of claim 42, wherein the unsegmented surface includes at least a portion of: a reflective optic, a laser window, a vacuum chamber window, or an optical filter.

52. A system, comprising:
a vacuum chamber configured to contain a target material, wherein a plasma is generated in response to an excitation of the target material; and
one or more outlets configured to receive gas flowing from a fluidically coupled gas source, the one or more outlets being further configured to actively flow the gas towards a source of debris and away from a surface at a controlled flow rate, wherein the surface includes a substantially transparent layer disposed adjacent to a surface layer, wherein the one or more outlets are configured to flow the gas through a plurality of openings formed in the substantially transparent layer.

53. An illumination system, comprising:
a target material;
an excitation source configured to generate an illumination beam to irradiate the target material to generate a plasma;
an unsegmented collector optic, the unsegmented collector optic including one or more openings formed in a reflective surface of the unsegmented collector optic, the unsegmented collector optic being configured to reflect illumination emanating from the plasma towards an illumination delivery path, wherein the illumination beam from the excitation source propagates through one opening of the one or more openings to irradiate the target material to generate the plasma;
a gas source configured to actively flow gas through the one or more openings formed in the reflective surface of the unsegmented collector optic towards a source of debris at a controlled flow rate and away from the reflective surface of the unsegmented collector optic, wherein the two or more openings are configured to provide two or more expanding streams of the gas flowing away from the reflective surface of the unsegmented collector optic, wherein the two or more openings are distributed across the reflective surface such that at least two expanding streams of the gas of the two or more expanding streams of the gas overlap; and
a tubular structure bounding an outer edge of the reflective surface of the unsegmented collector optic, the tubular structure being configured to prevent the gas from expanding outwards beyond the outer edge of the reflective surface of the unsegmented collector optic.

54. The illumination system of claim 53, wherein the one or more openings are distributed in an array across the reflective surface of the unsegmented reflective optic.

* * * * *